United States Patent
Vinding-Diers

(10) Patent No.: US 6,174,066 B1
(45) Date of Patent: Jan. 16, 2001

(54) LIGHT DEVICE FOR VERIFYING THE POSSIBLE PRESENCE OF SOLID DEPOSITS AND OTHER IMPURITIES INSIDE A BOTTLE OF WINE

(76) Inventor: Anders Vinding-Diers, #30 P. Del Monte, Di Pleta, 001876 Rome (IT)

( * ) Notice: Under 35 U.S.C. 154(b), the term of this patent shall be extended for 0 days.

(21) Appl. No.: 09/266,598

(22) Filed: Mar. 11, 1999

(51) Int. Cl.$^7$ ................................................. F21N 131/00
(52) U.S. Cl. ............................ 362/96; 362/101; 362/154
(58) Field of Search ............................. 362/96, 101, 154, 362/562

(56) References Cited

U.S. PATENT DOCUMENTS

| | | | |
|---|---|---|---|
| 2,259,394 | * 10/1941 | Sachtleben | 362/562 X |
| 2,547,450 | * 4/1951 | Du Pont | 362/96 X |
| 2,596,357 | * 5/1952 | Coleman | 362/96 X |
| 3,610,762 | * 10/1971 | Dugan | 362/101 X |
| 5,307,250 | * 4/1994 | Pearson | 362/101 |

FOREIGN PATENT DOCUMENTS

10956485 * 12/1960 (DE) ..................................... 362/101

* cited by examiner

Primary Examiner—Laura K. Tso
(74) Attorney, Agent, or Firm—Dykema Gossett PLLC

(57) ABSTRACT

The invention concerns a light device capable of being slipped from the top downward onto upper part of a wine bottle and fitting against the shoulder of the said bottle; the device has a small lamp, powered by a battery, which is capable of producing a cone of light aimed through the glass inside the bottle to light the wine contained therein during the decanting operation, in order to permit instantaneous verification of the presence of any possible impurities in suspension.

11 Claims, 1 Drawing Sheet

LIGHT DEVICE FOR VERIFYING THE POSSIBLE PRESENCE OF SOLID DEPOSITS AND OTHER IMPURITIES INSIDE A BOTTLE OF WINE

BACKGROUND OF THE INVENTION

The subject of this patent application for an industrial invention is a light device to be mounted on a bottle of wine in order to verify the possible presence inside it of solid deposits or other impurities.

It is not uncommon for certain wines, particularly red wines subjected to aging, to produce solid deposits in the form of small irregular fairly dark colored plates.

As long as a bottle of such a wine remains in an upright position, the aforesaid deposits tend to lie on the bottom of the bottle; however, the turbulence created inside the bottle during wine decanting agitates said solid deposits causing the particles to become suspended in the wine.

This circumstance naturally calls for a considerable amount of caution during the wine decanting in order to prevent particles from becoming carried into the glass. It is evident, in fact, that the presence in the glass of such particles significantly compromises the appearance of the wine itself (which is so important to connoisseurs); destroys the taste and spoils the enjoyment, particularly when the person holding the glass is not aware of their presence.

The method that is commonly used today to prevent said solid deposits from being decanted along with the wine is to avoid pouring out the last amount of the wine contained in the bottle. In this manner one seeks to avoid these turbulences near the bottom of the bottle, the most vulnerable area since it is most likely to cause agitation of the said solid particles.

Given these considerations, it is desirable to know before decanting a bottle whether or not the wine inside it contains the solid particles in suspension. This determination would dictate the way in which manner the decanting is to be done.

In the absence of deposits, all the wine may be poured out entirely and quickly. On the other hand, if the deposits are present, the wine must be poured very slowly and the bottle must not be completely emptied.

In practice, however, determination of the presence of possible solid particles remains complicated due to the fact that today all the highly esteemed wines are bottled in dark glass. This circumstance makes it fairly difficult to actually determine with certainty whether or not the wine contains solid particles in suspension.

In order to make such verification today, a bottle of wine is usually held up to an artificial light source or to the sun. It should be noted in the regard that this type of verification is rather empirical and its results are approximate. Also, it cannot easily be performed during the operation of pouring the wine into a glass to monitor decanting process.

Sometimes, the flame of a candle is placed next to a bottle during the decanting operation. However, the flame presents the disadvantage of blackening the glass of the bottle; and it requires skill to decant with a candle.

It is also important to note that while the need to ascertain the possible presence of impurities and solid particles in suspension is manifested primarily with reference to red wines, it is nonetheless true that at times there could be an interest in performing the same type of examination on white wines, particularly in dark glass bottles. This is true despite the fact that the probability of the formation of deposits or impurities in white wine is lower than in aged red wines.

SUMMARY OF INVENTION

The present invention provides a light device capable of being mounted to a bottle of wine so as to fit on the shoulder thereof. During decanting, a light beam aimed directly at the wine contained in the bottle permits the immediate and unequivocal verification, by backlighting, of the possible presence of solid particles in suspension in the liquid mass.

The light beam, which is produced just below the neck of the bottle, allows the wine being poured to be examined in real time during decanting. This makes it possible to suspend the pouring operation as soon as it is determined that solid particles in the liquid wine are coming too close to the shoulder and neck of the bottle, thereby avoiding the risk of being carried over into the glass.

BRIEF DESCRIPTION OF THE DRAWINGS

For greater clarity, the description of the invention will be explained with reference to the attached drawings, provided by way of nonrestrictive illustration only, where.

DESCRIPTION OF THE INVENTION

Figure 2:
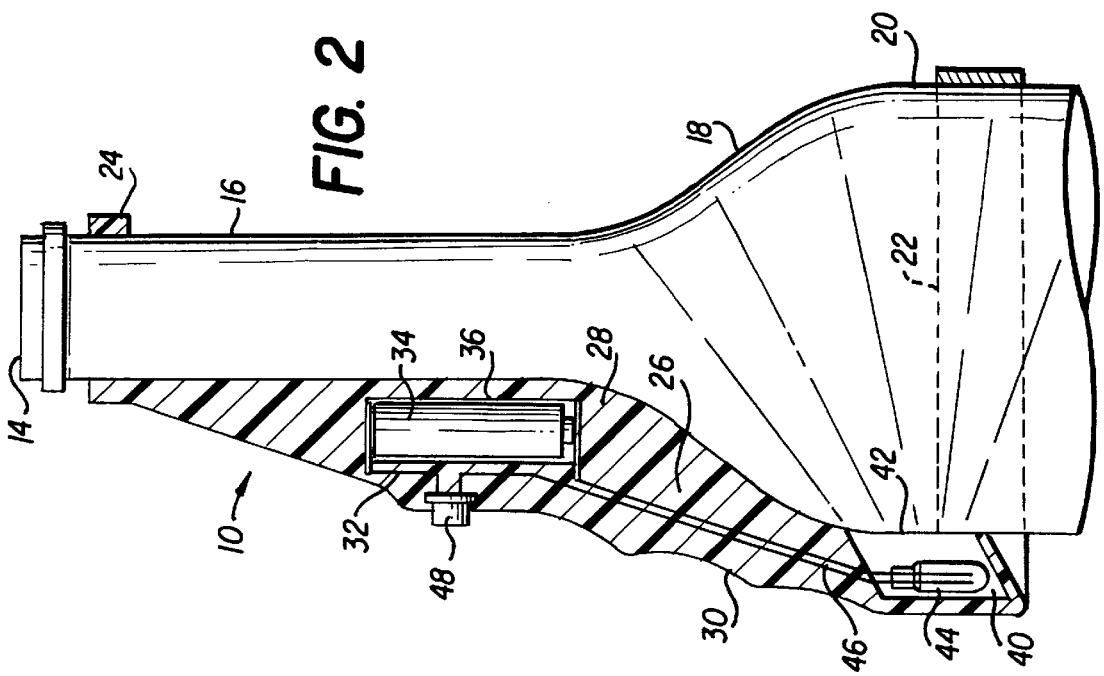
FIG. 2 is a fragmentary side sectional view of the device shown in FIG. 1.

With reference to said drawings, the invention comprises a lighted handgrip 10 positioned on a wine bottle 12 having an open end 14, a neck 16, a shoulder 18 and body 20. The hand grip 10 has a strap 22 capable of surrounding the body 20 of the bottle 12 below the shoulder 18. The hand grip 10 has an upper collar 24 capable of slipping over the neck 12 of the said bottle at the open end 14 as shown. The strap 12 and upper collar 24 are connected by a handle 26.

Figure 1:
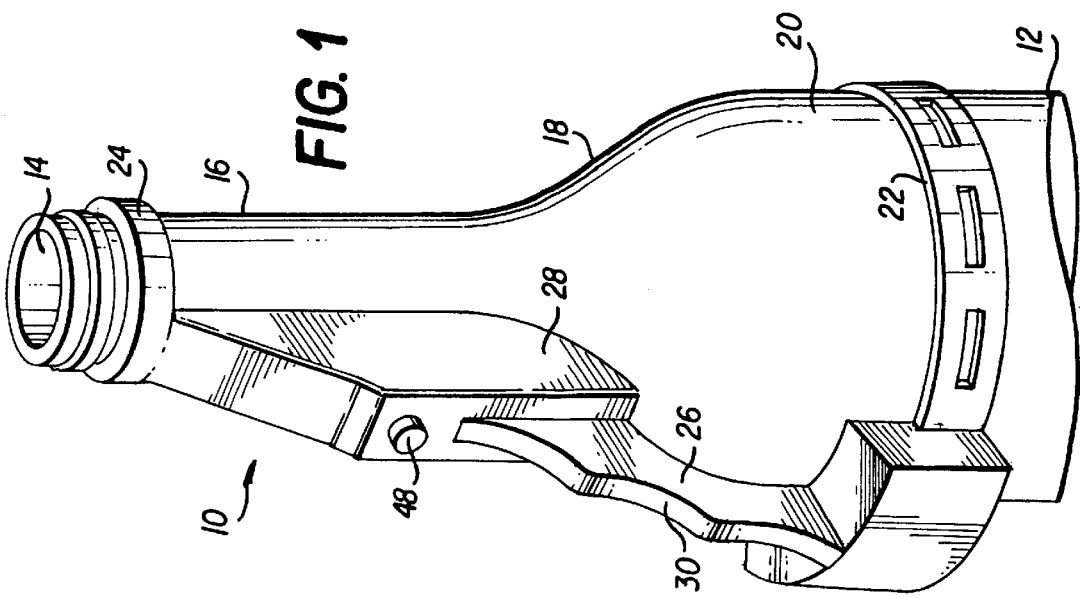
FIG. 1 is an perspective representation of the device according to the invention installed on a bottle.

This handgrip 10 may be installed over the top 14 of the wine bottle 12 by an energetic push from the top downward, as shown in FIG. 1. The handle 26 has a back surface 28 with a profile shaped so as to fit against the outer profile of the shoulder 18 and neck 16 of the bottle 12 in generally confronting relation. The engagement between the shaped back surface 28 and the bottle 12 constitutes, for the device according to the invention, a point of abutment or stop, wherein a close fit with the said bottle is achieved.

The handgrip 10 has a fingergrip or crest 30 which may be grasped, during the wine pouring operation, by the fingers of the user. The palm of the hand rests against the shoulder 18 and neck 16 of the bottle opposite the crest 30.

A box-like compartment 32 is located intermediate the crest 30 and the top collar 24 and houses a small sized battery 34, for example, of the type used in cameras. The battery 34 may be installed through a suitable door or opening 36 is the underside of the housing.

The housing 10 has a lamp chamber 40 located at the distal end thereof near the strap 22. The chamber 40 has a window 42 on the underside thereof which is in confronting relation with the body 20 of the bottle 12 below the shoulder 18 as shown. The chamber 40 houses a lamp 44.

The lamp 40 is powered by the battery 34 by means of interconnecting electric wire leads 46 running inside a suitable conduit cut into the back of the said crest 30. The lamp 44 is turned on and off by means of a button switch 48 provided on the front of the box-like compartment or chamber 32 housing the battery 34. The switch 48 may be a spring loaded normally open switch which is operable by the finger of the user during decanting.

The lamp 44 is turned on during the operation of decanting the wine contained in the bottle. When energized, the light bulb 44 produces a cone of light 50 which illuminates the interior of the bottle and the fluid stream and makes it possible to determine by backlighting the possible presence of any impurities present in suspension in the wine as it flows out.

It is apparent, moreover, that the device 10 also has the benefit of being interchangeable, because once the wine has been poured from one bottle 12, it may be removed from that bottle, by simply pulling it upward, and it may be mounted onto a new bottle to be decanted over the neck 16.

I claim:

1. A device for use in illuminating the contents of a fluid stream exiting a wine bottle, the wine bottle having an elongated neck portion, a body portion and a curved shoulder portion extending between the neck and the body portions, said device comprising:

a light emitting element;

a power cell operatively connected to said light emitting element;

a switch for activating and deactivating said light emitting element;

said power cell and said light emitting element being contained within a housing structure which attaches to said bottle, said housing structure including an exterior surface for contacting the hand of a user and an internal surface for disposition in opposing relation to the bottle surface such that upon activation of the light emitting element, the interior of the bottle at the curved shoulder portion is illuminated, and wherein said power cell and said light emitting element are contained within separate compartments within the housing structure.

2. The invention according to claim 1, wherein the interior surface of the housing structure opposing said bottle surface has a profile substantially corresponding to the profile of the bottle.

3. The invention according to claim 2, wherein the exterior surface of the housing structure comprises a crested profile for engaging the fingers of a user.

4. A device for use in illuminating the contents of a fluid stream exiting a wine bottle, the wine bottle having an elongated neck portion, a body portion and a curved shoulder portion extending between the neck and the body portions, said device comprising:

a light emitting element;

a power cell operatively connected to said light emitting element;

a switch for activating and deactivating said light emitting element;

said power cell and said light emitting element being contained within a housing structure which attaches to said bottle, said housing structure including an exterior surface for contacting the hand of a user and an internal surface for disposition in opposing relation to the bottle surface such that upon activation of the light emitting element, the interior of the bottle at the curved shoulder portion is illuminated, and a strap for surrounding the body of said bottle.

5. A light device for use in illuminating the contents of a fluid stream exiting a wine bottle, the bottle having an elongated neck portion, a body portion and a curved shoulder portion extending between and connecting said neck and body portions; said light device comprising:

a light emitting element;

a power cell operatively connected to said light emitting element;

a switch for activating and deactivating said light emitting element;

said light emitting element, said power cell and said switch being contained within a profiled housing structure comprising a handgrip and a ring element for engaging the neck of said bottle such that upon activation of the light emitting element, the interior of the bottle at the curved shoulder portion is illuminated; and wherein said handgrip has a created profile for engaging the fingers of a user.

6. The invention according to claim 5, further comprising a strap for surrounding the body of said bottle.

7. A device operable by the hand of a user for use in illuminating the contents of a fluid stream exiting a wine bottle, the wine bottle having an elongated neck portion, a body portion and a curved shoulder portion defining a surface extending between the neck and the body portions, said device comprising:

a housing attachable to said bottle, said housing including an exterior surface engagable with the hand of the user and an internal surface for disposition in opposing relation to the bottle surface;

a light emitting element located in the housing;

a switch electrically connected to the light emitting element for activating and deactivating said light emitting element such that upon activation of the light emitting element, the interior of the bottle is illuminated; and a strap connected to the housing for surrounding the body of said bottle.

8. The invention according to claim 7 further including a power cell in circuit with the switch and said light emitting element for supplying power to the light upon activation of the switch.

9. The invention according to claim 7, wherein the interior surface of the housing opposing said bottle surface has a profile substantially corresponding to the profile of the bottle.

10. The invention according to claim 9, wherein the exterior surface of the housing structure comprises a crested profile for engaging the fingers of a user.

11. The invention according to claim 7, further comprising a collar connected to the housing for surrounding the neck of the bottle.

* * * * *